United States Patent
McGuinness et al.

(10) Patent No.: US 10,399,079 B2
(45) Date of Patent: Sep. 3, 2019

(54) DIAGNOSTIC DEVICE

(71) Applicant: Hewlett-Packard Development Company, L.P., Houston, TX (US)

(72) Inventors: Nicholas McGuinness, San Diego, CA (US); Chantelle Domingue, Corvallis, OR (US); Manish Giri, Corvallis, OR (US); Jeremy Sells, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 15/546,735

(22) PCT Filed: Jan. 30, 2015

(86) PCT No.: PCT/US2015/013752
§ 371 (c)(1),
(2) Date: Jul. 27, 2017

(87) PCT Pub. No.: WO2016/122588
PCT Pub. Date: Aug. 4, 2016

(65) Prior Publication Data
US 2018/0015457 A1    Jan. 18, 2018

(51) Int. Cl.
*B01L 3/00* (2006.01)
*G01N 27/07* (2006.01)
*G01N 33/487* (2006.01)

(52) U.S. Cl.
CPC ..... *B01L 3/50273* (2013.01); *B01L 3/502715* (2013.01); *B01L 2200/10* (2013.01);
(Continued)

(58) Field of Classification Search
CPC .... B01L 3/50273; B01L 3/5027; B01L 3/502; B01L 3/50; B01L 3/00; B01L 2200/10; B01L 2300/023; B01L 2300/024; B01L 2300/02; B01L 2300/00
USPC .......................................... 422/502, 500, 50
See application file for complete search history.

(56) References Cited

U.S. PATENT DOCUMENTS

2001/0039059 A1    11/2001   Freitag et al.
2002/0045265 A1*    4/2002   Bergh ....................... B01J 4/00
                                                              436/37

(Continued)

FOREIGN PATENT DOCUMENTS

JP      2002153770      5/2002
JP      2006517029      7/2006
WO      WO-2014178827   11/2014

OTHER PUBLICATIONS

Chin et al.; Low-cost Microdevices for Point-of-care Testing; 2013.
(Continued)

*Primary Examiner* — Christine T Mui
(74) *Attorney, Agent, or Firm* — Fabian VanCott (57) ABSTRACT

A microfluidic diagnostic device may comprise a fluid inlet to receive a fluid from a fluidic slot, a main microfluidic channel fluidly coupled to the fluid inlet, and a main microfluidic pump interposed between the fluid inlet and the main microfluidic channel to continuously circulate a fluid through the fluidic slot, fluid inlet, and main microfluidic channel wherein the width of the fluid inlet is different from the width of the main microfluidic channel. A diagnostic device, comprising a fluidic slot, a fluid inlet fluidly coupled to the fluidic slot, a main channel fluidly coupled to the fluid inlet, and an inlet pump interposed between the fluid inlet and channel wherein the cross-sectional area of the fluid inlet is relatively larger at least one point than the cross-sectional area of the channel.

20 Claims, 6 Drawing Sheets

(52) U.S. Cl.
CPC ... *B01L 2300/023* (2013.01); *B01L 2300/024* (2013.01); *B01L 2300/027* (2013.01); *B01L 2300/0627* (2013.01); *B01L 2300/088* (2013.01); *B01L 2300/0816* (2013.01); *B01L 2300/0883* (2013.01); *B01L 2300/1827* (2013.01); *B01L 2400/0442* (2013.01); *B01L 2400/0487* (2013.01); *B01L 2400/086* (2013.01); *G01N 27/07* (2013.01); *G01N 33/48785* (2013.01)

(56) References Cited

U.S. PATENT DOCUMENTS

| | | |
|---|---|---|
| 2005/0019898 A1 | 1/2005 | Adey et al. |
| 2005/0266393 A1 | 12/2005 | Baxter et al. |
| 2007/0267295 A1 | 11/2007 | Chang et al. |
| 2008/0085219 A1 | 4/2008 | Beebe et al. |
| 2009/0281460 A1 | 11/2009 | Lowery et al. |
| 2010/0267162 A1 | 10/2010 | Kartalov et al. |
| 2011/0151500 A1* | 6/2011 | Hosokawa ......... G01N 33/4905 435/29 |
| 2011/0286493 A1 | 11/2011 | Torniainen et al. |
| 2014/0087412 A1 | 3/2014 | Fouras et al. |
| 2016/0102283 A1* | 4/2016 | Ravin ................... C12M 23/20 435/174 |

OTHER PUBLICATIONS

McGuinness et al., Microfluidic Sensing Device, Appln. No. PCT/US2014/137848; Filed Jan. 30, 2014.

* cited by examiner

DIAGNOSTIC DEVICE

BACKGROUND

Infectious diseases and other medical conditions affect life on a continual basis. Developments have been made to detect the presence of, for example, antigens in blood or other fluids in order to diagnose illnesses. In some cases, a microfluidic device is used to analyze an analyte within a fluid such as blood.

BRIEF DESCRIPTION OF THE DRAWINGS

The accompanying drawings illustrate various examples of the principles described herein and are a part of the specification. The illustrated examples are given merely for illustration, and do not limit the scope of the claims.

Throughout the drawings, identical reference numbers designate similar, but not necessarily identical, elements.

DETAILED DESCRIPTION

As mentioned above, microfluidic devices such as a microfluidic diagnostic chip (MDC) may be used to analyze a fluid including an analyte for pathogens or other components in a fluidic sample. During an analysis of an analyte in the MDC, large external pumps may be used to push the fluid including the analyte through the microfluidic channels defined therein. The large external pumps may, for example, use a large amount of power, are costly, and take up a large amount of room. Additionally, they may, for example, not portable leaving a patient with the option to come in to a lab or office to get tested.

The present specification, therefore describes an example microfluidic diagnostic device that may include a fluid inlet to receive a fluid from a fluidic slot, a main microfluidic channel fluidly coupled to the fluid inlet, and a main microfluidic pump interposed between the fluid inlet and the main microfluidic channel to continuously circulate a fluid through the fluidic slot, fluid inlet, and main microfluidic channel wherein the width of the fluid inlet is different from the width of the main microfluidic channel.

The present specification further describes an example diagnostic device including a fluidic slot, a fluid inlet fluidly coupled to the fluidic slot, a main channel fluidly coupled to the fluid inlet, and an inlet pump interposed between the fluid inlet and channel wherein the cross-sectional area of the fluid inlet is relatively larger at least one point than the cross-sectional area of the channel.

The present specification further describes a microfluidic chip, including a fluidic slot to receive a fluid including an analyte, a fluid inlet having a cross-sectional area tapering to a main channel, the fluid inlet including a number of baffles defined therein, a main pump placed between the fluid inlet and main channel, a secondary channel fluidly coupled to the main channel at both ends, and a secondary pump in the secondary channel wherein the main and secondary pumps are to the fluid through the main and secondary channels through alternating activation of the main and secondary pumps.

In the present specification and in the appended claims, the term "fluid" is meant to be understood broadly as any substance that continually deforms (flows) under an applied shear stress. In another example, a fluid includes a reagent or reactant. In another example, a fluid includes an analyte and a reagent or reactant. In still another example, a fluid includes an analyte, a reagent or reactant, among others.

Additionally, as used in the present specification and in the appended claims, the term "analyte" is meant to be understood as any substance within a fluid that may be placed in a microfluidic diagnostic chip (MDC) the is to be analyzed. In one example, an analyte may be any constituent substance within a fluid such as, but not limited to, animal or human blood, animal or human urine, animal or human feces, animal or human mucus, animal or human saliva, or yeast, among others.

Further, in the present specification and in the appended claims the term "reagent" is meant to be understood as a substance or compound that is added to a system in order to bring about a chemical reaction, or added to see if a reaction occurs. A reactant is meant to be understood as a substance that is consumed in the course of a chemical reaction.

Still further, as used in the present specification and in the appended claims, the term "a number of" or similar language is meant to be understood broadly as any positive number including 1 to infinity.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an example" or similar language means that a particular feature, structure, or characteristic described in connection with that example is included as described, but may not be included in other examples.

Figure 1:
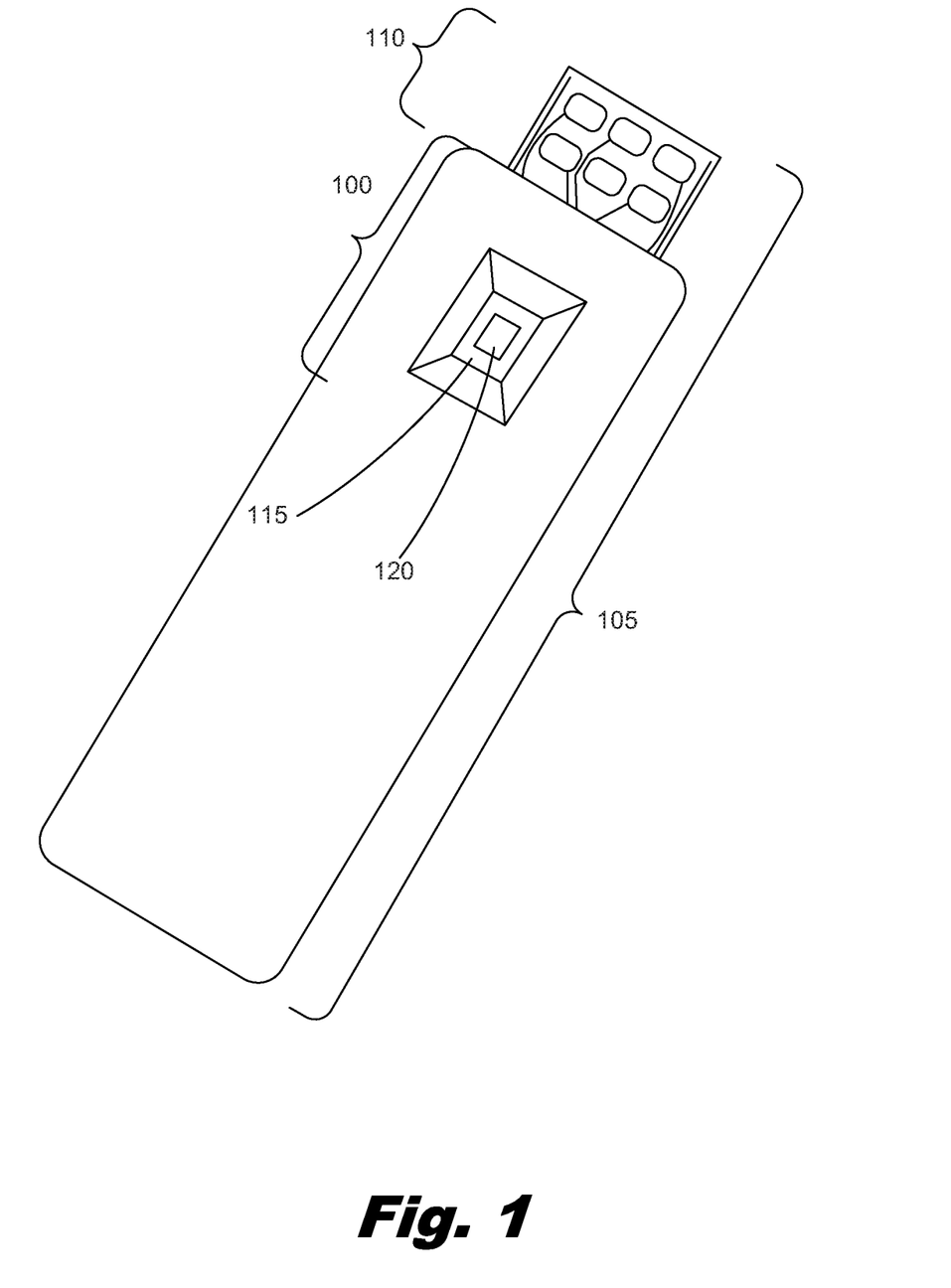
FIG. 1 is a diagram of a microfluidic diagnostic chip incorporated into a cassette for analyzing an analyte according to one example of the principles described herein.

Turning now to the figures, FIG. 1 is a diagram of a microfluidic diagnostic chip (100) incorporated into a cassette (105) for analyzing an analyte according to one example of the principles described herein. In the example shown in FIG. 1, the MDC (100) is included as part of a cassette (105). The cassette (105) further includes an electronic device interface (110) coupled to the MDC (100). The interface may allow the MDC (100) to receive instructions and power from an external source such as a computing device. In this example, the MDC (100) is the part of the cassette (105) that receives a fluid including an analyte while the cassette (105) and electronic device interface (110) provide the physical body to house the MDC and the power and instructions to operate the MDC respectively.

The cassette (105) may serve as a housing into which the MDC (100) and electronic device interface (110) are housed and protected from contamination and damage. The cassette (105) may also serve as a structure onto which a user may apply pressure in order to connect the electronic device interface (110) to an electronic device, for example directly to a computing device or to a connector that can be attached to a computing device.

The electronic device interface (110) may be any electrical contact points that may interface with an input/output port of an electronic device. In one example, the electronic device interface (110) is a universal serial bus (USB) interface capable of electrically coupling to a USB port in an electronic device. In other examples, the electrical contact points of the electronic device interface (110) may be defined to fit into a PCI bus, a PCIE bus, a SAS bus, and a SATA bus, among others. In one example, the electronic device interface (110) may include electrical contact points that interface with a specialized port in a specialized computing device.

The MDC (100) may include a feed tray (115) into which a fluid including an analyte is placed. The feed tray (115) directs the fluid into a fluidic slot (120) of the MDC (100). During operation, the fluid is placed in the feed tray (115) and passed into the fluidic slot (120). When the fluid is in the fluidic slot (120) the MDC (100) receives electrical power from an electrical device via the electronic device interface (110).

The MDC (100) may further include a number of sensors located in a number of microfluidic channels defined in the MDC (100). In one example, the sensors are impedance sensors capable of measuring an impedance value of an analyte in a fluid as the analyte is presented over the sensor. These sensors may measure the impedance of the analyte over time as well as measure the changes of the impedance value over time.

The MDC (100) may further include a number of pumps located in a number of microfluidic channels defined in the MDC (100). The pumps are thin film resistors that, when a voltage is applied to them, nucleate a bubble at the surface of the thin film in contact with the fluid. The thin film resistor may be made of, for example, tantalum, platinum, gold, silicon carbide, silicon nitride, tungsten, or combinations thereof. The rapid Joule heating of the thin-film resistor superheats the fluid in intimate contact with a thin film resistor. In one example, the pumps are encapsulated with a passive film and a cavitation film. This drive bubble forms on the cavitation film over the passive film and resistor. During operation of the pump, a voltage is applied to the resistor at a certain rate. In one example, the voltage applied may be applied at a rate of 1-100 kHz and may range from 5-35V. In other examples, the voltage may be greater that 35V or less than 5V and may be applied at different frequencies. The drive bubble is thus created and collapses which constitutes the pumping mechanism by which the fluid is passed through the microfluidic channels.

Figure 2A:
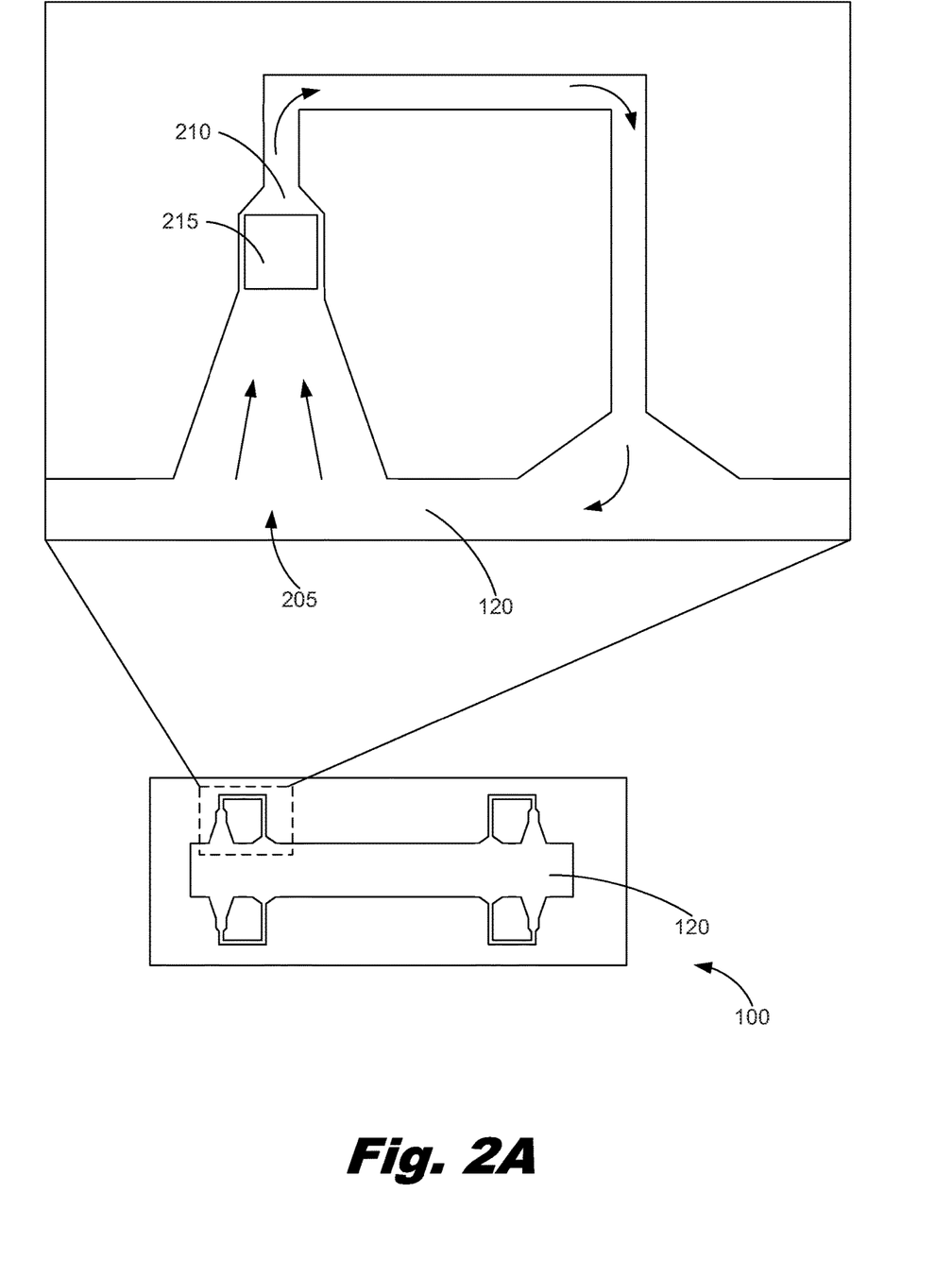
FIG. 2A is a block diagram of a microfluidic diagnostic chip for analyzing an analyte while recirculating a fluid including the analyte according to one example of the principles described herein.
Figure 2B:
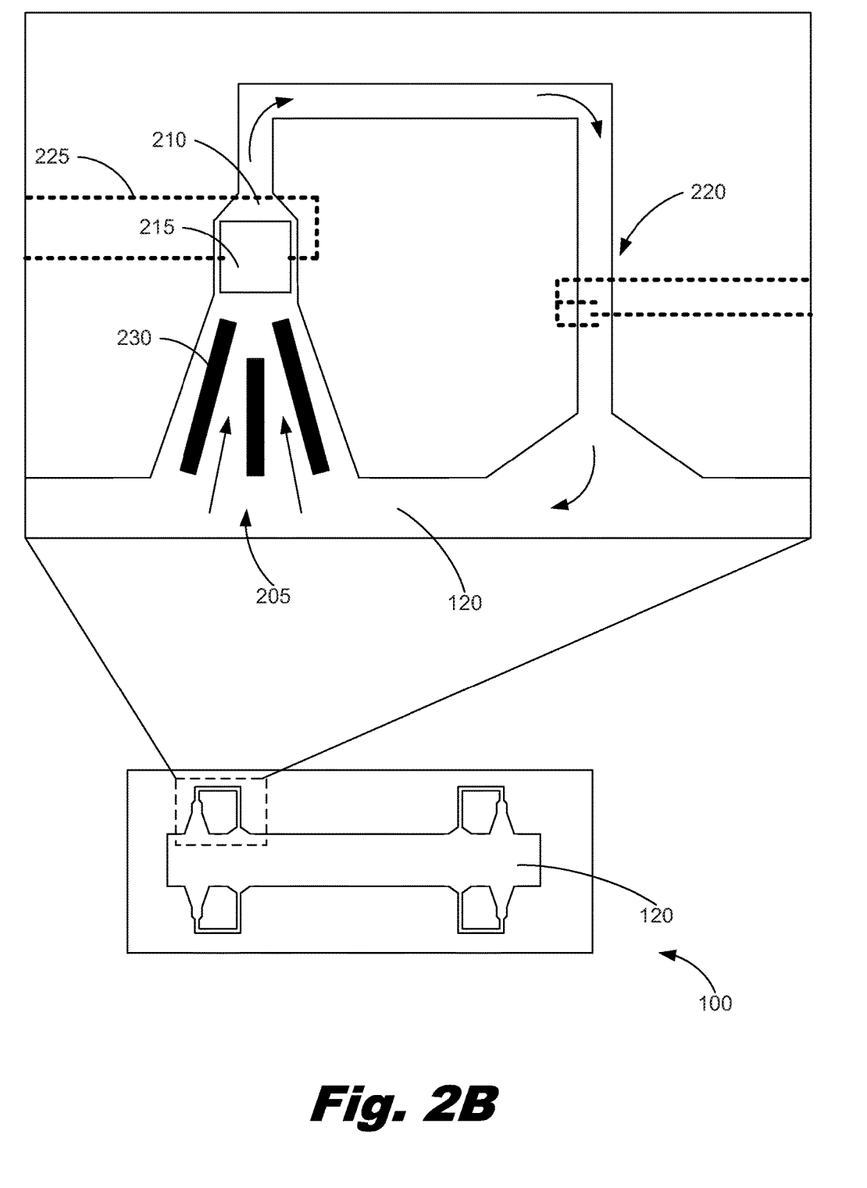
FIG. 2B is a block diagram of a microfluidic diagnostic chip for analyzing an analyte while recirculating a fluid including the analyte according to another example of the principles described herein.

FIG. 2A is a block diagram of a microfluidic diagnostic chip (MDC) (100) for analyzing an analyte while recirculating a fluid including the analyte according to one example of the principles described herein. The MDC (100) in FIG. 2A may include a fluidic slot (120), a microfluidic channel inlet (205), a microfluidic channel (210), and a microfluidic pump (215). FIG. 2B is similarly a block diagram of a microfluidic diagnostic chip (MDC) (100) for analyzing an analyte while recirculating a fluid including the analyte according to another example of the principles described herein. The MDC (100) in FIG. 2B may include the fluidic slot (120), the microfluidic channel inlet (205), the microfluidic channel (210), and the microfluidic pump (215) shown in FIG. 2A as well as a sensor (220) and a number of baffles (230). The MDC (100) will now be described with reference to FIGS. 2A and 2B.

The microfluidic, channel inlet (205), microfluidic channel (210), microfluidic pump (215), and sensor (220) may cooperate together to recirculate a fluid deposited into the fluidic slot (120).

The fluidic slot (120) may be fluidly coupled to at least the microfluidic channel inlet (205) and may be defined into the substrate of which the MDC (100) is built. In one example, the substrate is made of silicon and the fluidic slot (120) is created by, for example, via sand blasting, laser etching, dry etching, wet etching, or combinations thereof. In one example, the fluid to be analyzed by the MDC (100) may be fed into the fluidic slot (120) via the feed tray (115) using gravity. Additionally, the fluidic slot (120) may fill up with fluid before spilling over into the microfluidic channel inlet (205) and passed into the microfluidic channel inlet (205) and main microfluidic channel (210) using capillary forces, surface tension, viscous forces, pressure gradients, diffusion dominance, among others. In this example, the microfluidic channel inlet (205) is fluidly coupled to an upper portion of the fluidic slot (120). During a recirculation process where the fluid is recirculated, the fluidic slot (120) may maintain a portion of the fluid such that it may supply an amount of fluid including the analyte to the microfluidic channel inlet (205) as an amount of analyte is reintroduced into the fluidic slot (120) during the recirculation.

Figure 3:
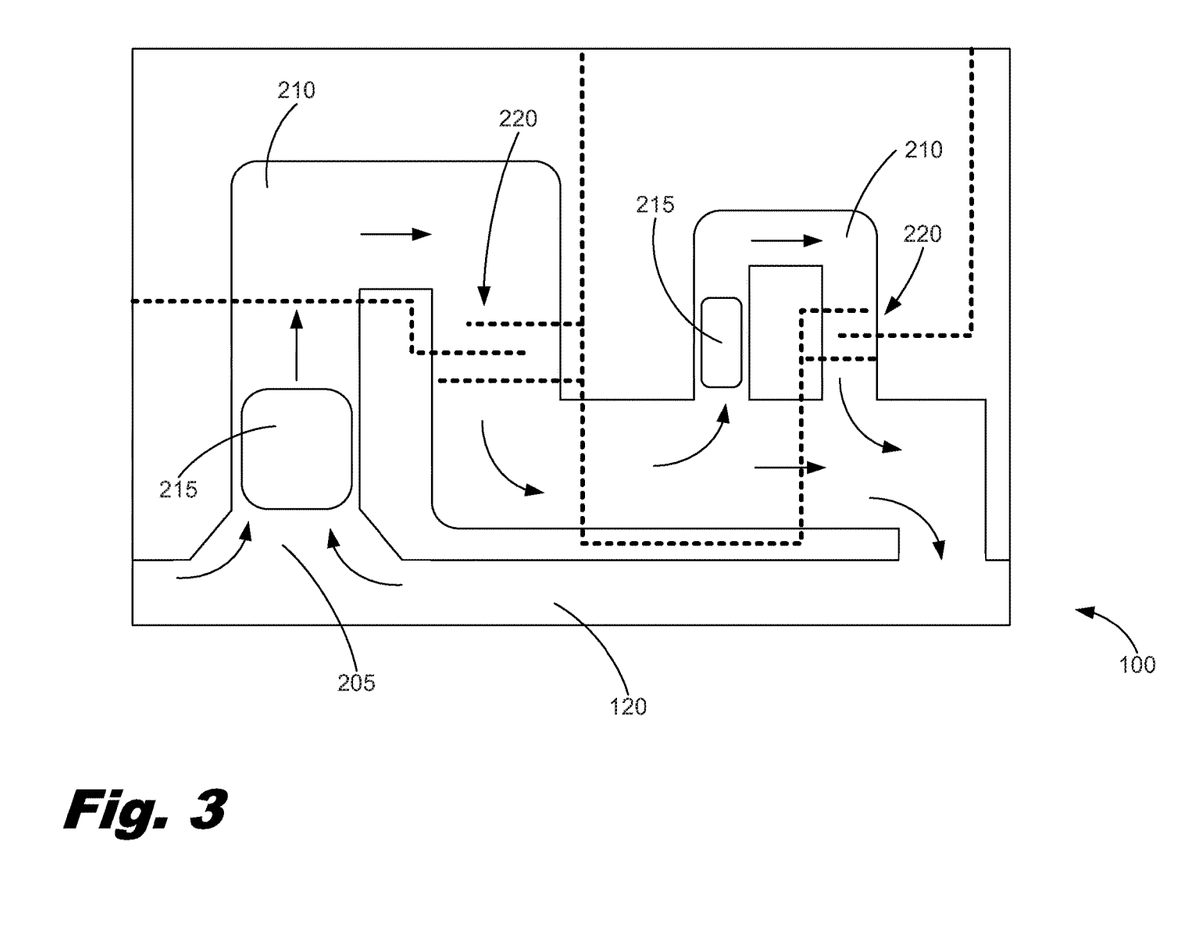
FIG. 3 is a block diagram of a microfluidic diagnostic chip for analyzing an analyte while recirculating a fluid including the analyte according to another example of the principles described herein.

The microfluidic channel inlet (205) may fluidly connect the fluidic slot (120) with the microfluidic channel (210). In one example, the microfluidic channel inlet (205) has a width or cross-sectional area that is wider than the microfluidic channel (210). In another example, the microfluidic channel inlet (205) may have a width that is larger than the microfluidic channel (210) but that tappers down to the width of the microfluidic channel (210). In this example, the tapering may be a gradual tapering or a step-wise tapering. Although FIGS. 2A-B and 3 show a microfluidic channel inlet (205) having a width that is greater than the microfluidic channel (210), the microfluidic channel (210) may have a width greater than that of the microfluidic channel inlet (205). As will be described below, the shape of the microfluidic channel inlet (205) as compared to the microfluidic channel (210) causes an asymmetry in the fluidics causing movement of the fluid in a certain direction when a pump is activated. Consequently, the present specification contemplates the use of any widths of microfluidic channel inlet (205) and microfluidic channel (210) such that a difference between the two creates the asymmetry in the fluidics described herein.

Between the microfluidic channel inlet (205) and the microfluidic channel (210), a microfluidic pump (215) is placed to pump the fluid through the system including the microfluidic channel inlet (205), microfluidic channel (210), and fluidic slot (120). The microfluidic pump (215) pumps the fluid as indicated by the arrows shown in FIG. 2. As described above the microfluidic pump (215) may include a resistor such as a thin film resistor. A number of electrical leads (225) provide power to the microfluidic pump (215). The microfluidic pump (215) may also include a passive film overlaying the thin film resistor and a cavitation film overlaying the passive film. The passive and cavitation film may provide thermal insulation and a physical barrier between the analyte/fluid and the thin film resistor of the microfluidic pump (215). In one example, the passive film may be made of SiC or SiN and may be approximately 500-2000 angstroms thick. In another example, the cavitation film may be made of tantalum or platinum and may be approximately 500-2000 angstroms thick.

During operation, the microfluidic pump (215) and microfluidic channel inlet (205) may cooperate together to drive the fluid through the microfluidic channel (210). In one example, the microfluidic channel inlet (205) is so shaped so as to prevent any stagnation of particles (i.e. the analyte) within the fluid. Specifically, the shape of the microfluidic, channel inlet (205) interacts with the drive bubble developed by the microfluidic pump (215) as the microfluidic pump (215) is activated. The shape of the microfluidic channel inlet (205) versus the microfluidic channel (210) causes an asymmetry in the fluidics. As the drive bubble is created on the microfluidic pump (215), the drive bubble will grow more significantly towards the microfluidic channel inlet (205). Conversely, the drive bubble grows less significantly towards the microfluidic channel (210). As a result the asymmetric fluidics is created where a low fluidic resistance and inductance is present in the microfluidic channel inlet (205) while a large fluidic resistance and inductance is present in the microfluidic channel (210). This imbalance in fluidic resistance and inductance between the fluid in the microfluidic channel inlet (205) and the fluid in the microfluidic channel (210) causes the fluid to move from the microfluidic channel inlet (205) and into the microfluidic channel (210) after the drive bubble has collapsed.

In one example, the size of the microfluidic pump (215) may be 5 to 10 μm square. In another example, the width of the microfluidic pump (215) may be 5 to 100 μm while the length may be 5-100 μm. In yet another example, the size of the microfluidic pump (215) may be about the width of a particle (i.e., analyte) in the fluid. In this example, the length of the microfluidic pump (215) may be increased or decreased in order to increase or decrease the size of the drive bubble to be created with the microfluidic pump (215).

The widths of the microfluidic channel (210) and microfluidic channel inlet (205) may vary depending on a number of factors including the particle size of the analyte in the fluid, the desired density of particles, and the desired flow rate of the particles in the fluid, among others. In the present specification, however, the microfluidic channel inlet (205) has a width greater than the microfluidic channel (210) so as to produce the asymmetric fluidic resistance and inductance as described above. In one example, the width of the microfluidic channel (210) may be the width of an individual particle such as a blood cell. In this example, the microfluidic channel (210) permits a single cell to pass through it one at a time. This advantageously provides for a relatively high signal to noise ration during sensing of the particles.

The MDC (100) may further include a sensor (220) to analyze the analyte. In one example the sensor (220) measures the impedance of the fluid including an analyte as it is presented over the sensor (220). In this example, the fluid may be a blood sample including a number of blood cells (i.e. analyte) to be counted or otherwise analyzed. The flow of the fluid including the analyte through the microfluidic channel inlet (205), microfluidic channel (210), and fluidic slot (120) causes, in this example, the blood sample to be recirculated and potentially mixed with, for example, a reactant as the recirculation continues. The sensor (220) may, in one example, measure the concentration of particles (cells) in the fluid as compared to the reactant. This may allow the MDC (100) to measure and obtain a proper concentration of an analyte and reactant before, for example, analyzing it further or mixing it with further reactants or fluids.

The microfluidic channel inlet (205) may include a number of baffles (230) defined therein. The baffles (230) may serve to prevent eddy currents and fluidic dead zones from forming within the microfluidic channel inlet (205) or other fluid paths. Additionally, the baffles (230) may align the particles within the fluid in order to align them in preparation to fit through the microfluidic channel (210). The baffles (230) may be placed in the MDC (100) by coupling the baffles (230) to either a primer layer deposited on the silicon substrate or directly on a dielectric film such as silicon carbide.

FIG. 3 is a block diagram of a MDC (100) for analyzing an analyte while recirculating a fluid including the analyte according to another example of the principles described herein. The MDC (100) of FIG. 3 may include similar elements as those shown in FIG. 2. In FIG. 3, however, the MDC (100) further includes an additional microfluidic pump (215) downstream of the first microfluidic pump (215) and located within a microfluidic channel (210) branching off from the main microfluidic channel (210). Although FIG. 3 shows two microfluidic pumps (215) in total, any plurality of microfluidic pumps (215) may be implemented. The second or additional microfluidic pumps (215) may cooperate with the first microfluidic pump (215) closest to the microfluidic channel inlet (205). During operation the first microfluidic pump (215) may be activated while the other microfluidic pumps (215) do not. After activating of the first microfluidic pump (215), the microfluidic pump (215) directly downstream of the first microfluidic pump (215) may then be activated. Any remaining microfluidic pumps (215) may be activated in a similar sequential order until all microfluidic pumps (215) have been activated whereupon the first microfluidic pump (215) then activates again repeating the sequential activation order. The sequential activation of each of the microfluidic pumps (215) creates a push-pull action such that the pumps cooperate with each other to create a constant flow of fluid including the analyte across the sensors.

In this multiple microfluidic pump (215) configuration, multiple sensors (220) may be used as well. The multiple sensors (220) may each detect whether there is an evolution in the concentration of the particles, reagents, and analyte in the fluid as the fluid is recirculated through the MDC (100). Although FIG. 3 shows two microfluidic pumps (215), the present specification contemplates the use of any number of microfluidic pumps (215).

Figure 4:
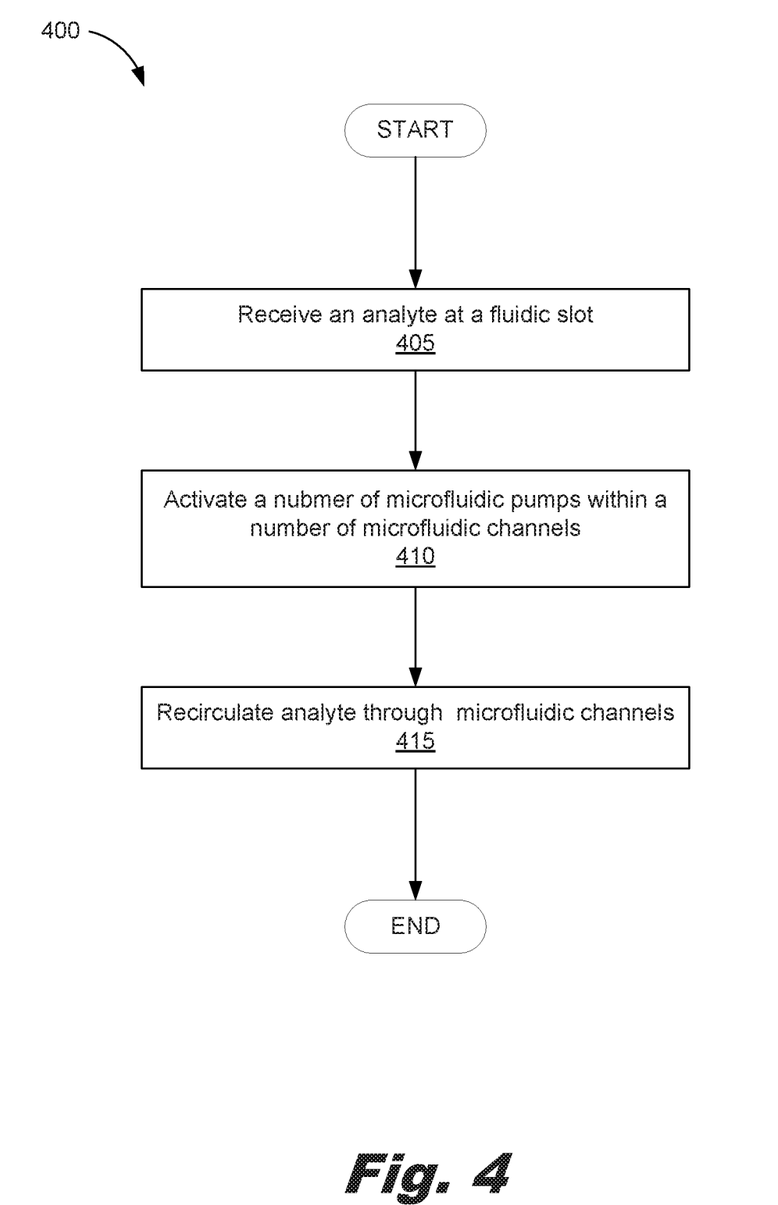
FIG. 4 is a flowchart showing a method of recirculating a fluid including an analyte through an MDC according to one example of the principles described herein.

FIG. 4 is a flowchart showing a method (400) of recirculating a fluid including the analyte through an MDC (100) according to one example of the principles described herein. The method (400) may begin with receiving a fluid including an analyte at a fluidic slot (120). As described above, the fluidic slot (120) is fluidly coupled to a microfluidic channel inlet (205). The microfluidic channel inlet (205) may further be fluidly coupled to a number of microfluidic channels (210) as described above in connection with FIGS. 2A-B and 3.

The method (400) may continue with activating (410) a number of microfluidic pumps (215) within the microfluidic channels (210). The first of the microfluidic pumps (215) to be activated may be the microfluidic pump (215) placed between the microfluidic channel inlet (205) and the microfluidic channel (210) as described above. Each subsequent microfluidic pump (215) may be sequentially activated following the initial microfluidic pump (215) being activated. The method then continues by recirculating (415) the fluid through the microfluidic channels (210) of the MDC (100). In other examples, any order of succession may be applied when activating the pumps arid the present specification contemplates the use of such alternative orders.

Once the fluid has been recirculated and mixed, it may be subject to additional analysis or chemical treatments before being ejected out of the MDC (100) and into a waste fluid reservoir located in the MDC (100) or cassette (105). The ejection of the waste fluid may be accomplished through the use of a bore defined in a microfluidic channel (210) and a microfluidic pump (215) coplanar to the bore. The bore is fluidly coupled to the reservoir such that activation of the microfluidic pump (215) coplanar to the bore will create its own drive bubble, pushing an amount of waste fluid through the bore.

Figure 5:
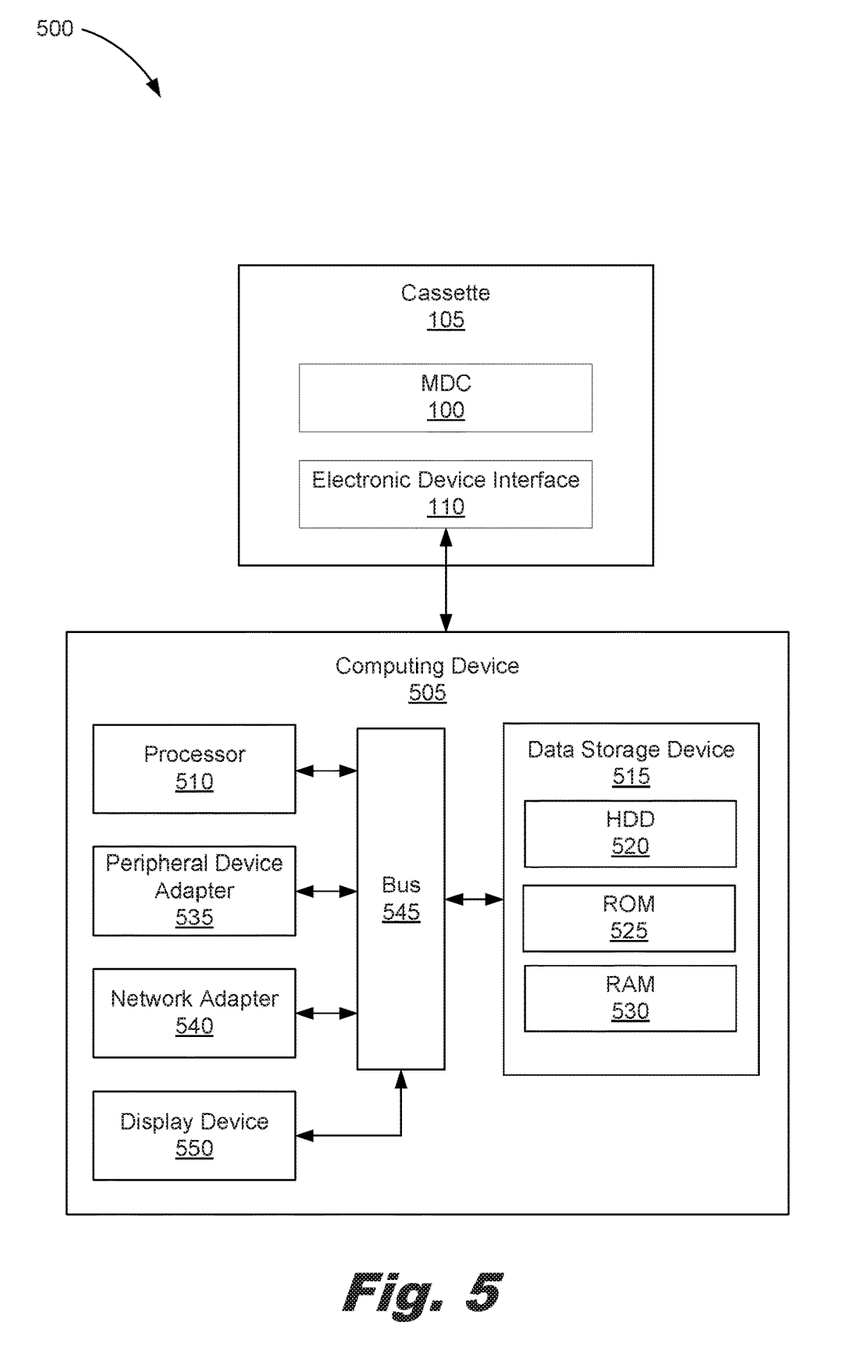
FIG. 5 is a block diagram of a microfluidic diagnostic chip system according to one example of the principles described herein.

FIG. 5 is a block diagram of a microfluidic diagnostic chip system (500) according to one example of the principles described herein. The system (500) includes a computing device (505) and a cassette (105) selectively electrically coupled to the computing device (505). The cassette (105) includes a MDC (100) and an electronic device interface (110) as described above in connection with FIG. 1. In one example, the cassette (105) may be communicatively coupled to the computing device (505) via a USB connector.

The computing device (505) includes various hardware components. Among these hardware components may be a number of processors (510), a number of data storage devices (515), a number of peripheral device adapters (535), a number of network adapters (540), and a display device (550). These hardware components may be interconnected through the use of a number of busses (545) and/or network connections. In one example, the processor (510), data storage device (515), peripheral device adapters (535), and network adapter (540) may be communicatively coupled via a bus (545).

The processor (510) may include the hardware architecture to retrieve executable code from the data storage device (515) and execute the executable code. The executable code may, when executed by the processor (510), cause the processor (510) to implement at least the functionality of receiving a number of electrical signals from the MDC (100) via the electronic device interface (110) and the peripheral device adapter (535), according to the methods of the present specification described herein. In the course of executing code, the processor (510) may receive input from and provide output to a number of the remaining hardware units.

The data storage device (515) may store data such as executable program code that is executed by the processor (510) or other processing device. The data storage device (515) may specifically store computer code representing a number of applications that the processor (510) executes to implement at least the functionality described herein.

The data storage device (515) may include various types of memory modules, including volatile and nonvolatile memory. For example, the data storage device (515) of the present example includes Random Access Memory (RAM) (530), Read Only Memory (ROM) (525), and Hard Disk Drive (HDD) memory (520). Many other types of memory may also be utilized, and the present specification contemplates the use of many varying type(s) of memory in the data storage device (515) as may suit a particular application of the principles described herein. In certain examples, different types of memory in the data storage device (515) may be used for different data storage needs. For example, in certain examples the processor (510) may boot from Read Only Memory (ROM) (525), maintain nonvolatile storage in the Hard Disk Drive (HDD) memory (520), and execute program code stored in Random Access Memory (RAM) (530).

Generally, the data storage device (515) may include a computer readable medium, a computer readable storage medium, or a non-transitory computer readable medium, among others. For example, the data storage device (515) may be, but not limited to, an electronic, magnetic, optical, electromagnetic, infrared, or semiconductor system, apparatus, or device, or any suitable combination of the foregoing. More specific examples of the computer readable storage medium may include, for example, the following: an electrical connection having a number of wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store computer usable program code for use by or in connection with an instruction execution system, apparatus, or device. In another example, a computer readable storage medium may be any non-transitory medium that can contain, or store a program for use by or in connection with an instruction execution system, apparatus, or device.

The hardware adapters (535, 540) in the computing device (505) enable the processor (510) to interface with various other hardware elements, external and internal to the computing device (505). For example, the peripheral device adapters (535) may provide an interface to input/output devices, such as, for example, display device (550), a mouse, or a keyboard. The peripheral device adapters (535) may also provide access to other external devices such as an external storage device, a number of network devices such as, for example, servers, switches, and routers, client devices, other types of computing devices, and combinations thereof.

The display device (550) may be provided to allow a user of the computing device (505) to interact with and implement the functionality of the computing device (505). The peripheral device adapters (535) may also create an interface between the processor (510) and the display device (550), a printer, or other media output devices. The network adapter (540) may provide an interface to other computing devices within, for example, a network, thereby enabling the transmission of data between the computing device (505) and other devices located within the network.

Aspects of the present system and method are described herein with reference to flowchart illustrations and/or block diagrams of methods, apparatus (systems) and computer program products according to examples of the principles described herein. Each block of the flowchart illustrations and block diagrams, and combinations of blocks in the flowchart illustrations and block diagrams, may be implemented by computer usable program code. The computer usable program code may be provided to a processor of a general purpose computer, special purpose computer, or other programmable data processing apparatus to produce a machine, such that the computer usable program code, when executed via, for example, the processor (510) of the computing device (505) or other programmable data processing apparatus, implement the functions or acts specified in the flowchart and/or block diagram block or blocks. In one example, the computer usable program code may be embodied within a computer readable storage medium; the computer readable storage medium being part of the computer program product. In one example, the computer readable storage medium is a non-transitory computer readable medium.

The specification and figures describe a diagnostic device to recirculate a fluid including an analyte. This diagnostic device may, in some examples, allow for the prevention of stagnation occurring within a microfluidic channel during circulation or recirculation of a fluid. The pumps described herein, may for example pump the fluid through a number of microfluidic channels such that the flow of fluid is continuous. The microfluidic channel inlet described herein may for example allow the fluid to flow continuously without any eddy currents forming by the pump or within the microfluidic channels. This may allow the analyte and reactants within the fluid to mix thoroughly. The constant recirculation of the fluid with the analytes and reagents may be monitored at the microfluidic level using impedance sensors to determine when the mixture has a homogenous consistency.

The preceding description has been presented to illustrate and describe examples of the principles described. This description is not intended to be exhaustive or to limit these principles to any precise configuration disclosed. Many modifications and variations are possible in light of the above teaching.

What is claimed is:

1. A microfluidic diagnostic device, comprising:
    a fluid inlet to receive a fluid from a fluidic slot, the fluid inlet comprising a plurality of linear baffles;
    a main microfluidic channel fluidly coupled to the fluid inlet; and
    a main microfluidic pump interposed between the fluid inlet and the main microfluidic channel to continuously circulate a fluid through the fluidic slot, fluid inlet, and main microfluidic channel,
    wherein the width of the fluid inlet is different from the width of the main microfluidic channel.

2. The microfluidic diagnostic device of claim 1, further comprising a secondary microfluidic channel extending from a portion of the main microfluidic channel and entering another portion of the main microfluidic channel.

3. The microfluidic diagnostic device of claim 2, wherein the secondary microfluidic channel comprises a secondary microfluidic pump to pull the fluid through the secondary microfluidic channel as the main microfluidic channel pumps.

4. The microfluidic diagnostic device of claim 2, wherein activation of the main microfluidic pump and the secondary microfluidic pump is to be alternated such that the main microfluidic pump is to push the fluid through the main microfluidic channel while the secondary microfluidic pump is to pull the fluid through the secondary microfluidic channel.

5. The microfluidic diagnostic device of claim 1, wherein the main microfluidic pump is a thin-film resistor and wherein application of a voltage to the thin-film resistor results in rapid nucleation of the fluid in contact with the thin-film resistor driving the fluid through the main microfluidic channel.

6. The microfluidic diagnostic device of claim 5, wherein a width of the main microfluidic pump is the same width as that of a human blood cell and wherein a length of the main microfluidic pump determines a size of a drive bubble.

7. A diagnostic device, comprising:
    a fluidic slot;
    a fluid inlet fluidly coupled to the fluidic slot, the fluid inlet comprising a plurality of baffles;
    a main channel fluidly coupled to the fluid inlet; and
    an inlet pump interposed between the fluid inlet and the main channel,
    wherein the cross-sectional area of the fluid inlet is relatively larger at at least one point than the cross-sectional area of the main channel.

8. The diagnostic device of claim 7, wherein a cross-sectional area of the fluid inlet tapers down to the cross-sectional area of the main channel.

9. The diagnostic device of claim 7, wherein the inlet pump is a thin-film resistor and wherein application of a voltage to the thin-film resistor results in a rapid nucleation of the fluid in contact with the thin-film resistor resulting in formation and collapse of a drive bubble that migrates the fluid through the main channel.

10. The diagnostic device of claim 9, wherein a width of the inlet pump is the same width as that of a human blood cell and wherein a size of the drive bubble depends on a length of the inlet pump.

11. The diagnostic device of claim 7, further comprising a secondary channel extending from a portion of the main channel and entering another portion of the main channel.

12. The diagnostic device of claim 7, wherein a secondary channel comprises a secondary channel pump to pull the fluid through the secondary channel as the main channel pumps.

13. A microfluidic chip, comprising:
    a fluidic slot to receive a fluid comprising an analyte;
    a fluid inlet having a cross-sectional area tapering to a main channel, the fluid inlet comprising a number of elongated baffles defined therein;
    a main pump placed between the fluid inlet and main channel;
    a secondary channel fluidly coupled to the main channel at both ends; and
    a secondary pump in the secondary channel,
    wherein the main and secondary pumps are to recirculate the fluid through the main and secondary channels through alternating activation of the main and secondary pumps.

14. The microfluidic chip of claim 13, further comprising a number of sensors to analyze the analyte.

15. The microfluidic chip of claim 14, further comprising a number of electrical connections to connect a computing device to the number of sensors and the main and secondary pumps.

16. The microfluidic diagnostic device of claim 1, wherein the fluid inlet comprising a plurality of linear baffles comprises at least three linear baffles.

17. The microfluidic diagnostic device of claim 1, wherein the linear baffles are sized to reduce eddies in adjacent fluid.

18. The diagnostic device of claim 7, wherein the plurality of baffles are a plurality of elongated baffles.

19. The microfluidic chip of claim 13, wherein the elongated baffles are linear, elongated baffles.

20. The microfluidic chip of claim 13, wherein the number of elongated baffles comprise a plurality of elongated baffles.

* * * * *

UNITED STATES PATENT AND TRADEMARK OFFICE
CERTIFICATE OF CORRECTION

PATENT NO.       : 10,399,079 B2
APPLICATION NO.  : 15/546735
DATED            : September 3, 2019
INVENTOR(S)      : Nicholas McGuinness et al.

It is certified that error appears in the above-identified patent and that said Letters Patent is hereby corrected as shown below:

In the Drawings

In sheet 5 of 6, FIG. 4, reference numeral 410, Line 1, delete "nubmer" and insert -- number --, therefor.

In the Claims

In Column 10, Line 9, in Claim 7, delete "at at least" and insert -- at least --, therefor.

Signed and Sealed this
Seventh Day of January, 2020

Andrei Iancu
*Director of the United States Patent and Trademark Office*